(12) United States Patent
Schelberger et al.

(10) Patent No.: US 6,291,497 B1
(45) Date of Patent: Sep. 18, 2001

(54) FUNGICIDAL MIXTURES

(75) Inventors: Klaus Schelberger, Gönnheim; Maria Scherer, Landau; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof; Reinhold Saur, Böhl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,859
(22) PCT Filed: May 13, 1998
(86) PCT No.: PCT/EP98/02822
  § 371 Date: Nov. 17, 1999
  § 102(e) Date: Nov. 17, 1999
(87) PCT Pub. No.: WO98/53684
  PCT Pub. Date: Dec. 3, 1998

(30) Foreign Application Priority Data

May 26, 1997 (DE) ............... 197 21 849
May 26, 1997 (DE) ............... 197 21 848

(51) Int. Cl.⁷ .................................. A01N 43/64
(52) U.S. Cl. ............ 514/384; 514/407; 514/520; 514/522; 514/539; 514/617; 514/619
(58) Field of Search ................. 514/384, 407, 514/539, 619, 520, 522, 617

(56) References Cited

U.S. PATENT DOCUMENTS 4,829,085  5/1989  Wenderoth et al. ............ 514/522
5,304,572  4/1994  Michelotti et al. ............ 514/514

FOREIGN PATENT DOCUMENTS 0254 426  1/1988 (EP) .

(List continued on next page.)

Primary Examiner—Allen J. Robinson
(74) Attorney, Agent, or Firm—Keil & Weinkauf

(57) ABSTRACT

A fungicidal mixture comprises
  a) a phenyl benzyl ether derivative of the formula I.a, I.b or I.c,

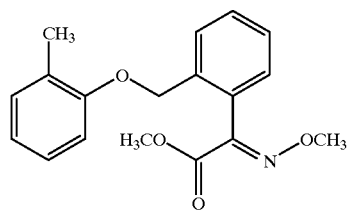
I.a

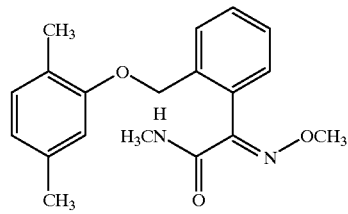
I.b

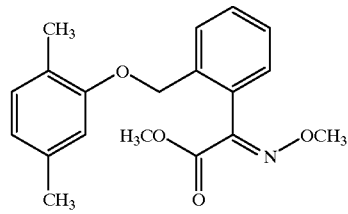
I.c and/or a carbamate of the formula Id

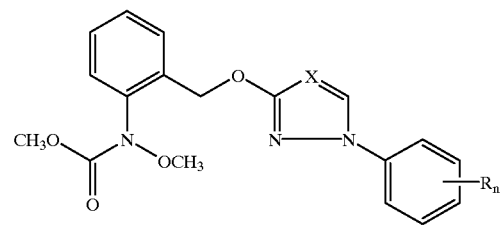
(Id)

where X is CH or N, n is 0, 1 or 2 and R is halogen, $C_1$–$C_4$-alkyl or $C_1$–$C_4$-haloalkyl, it being possible for the radicals R to be different if n is 2, or a salt or adduct thereof,
and
(b) a N-acetonylbenzamide of the formula II

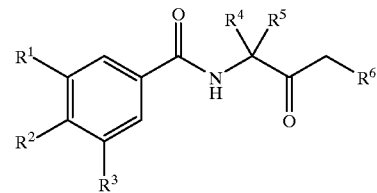
(II)

where:
  $R^1$ and $R^3$ independently of one another are each halogen or $C_1$–$C_4$-alkyl;
  $R^2$ is cyano, $C_1$–$C_4$-alkyl, $C_2$–$C_4$-alkenyl, $C_2$–$C_4$-alkynyl or $C_1$–$C_4$-alkoxy;
  $R^4$ is hydrogen or $C_1$–$C_4$-alkyl;
  $R^5$ is $C_2$–$C_4$-alkyl;
  $R^6$ is thiocyano, isothiocyano or halogen,
or a salt or adduct thereof,
in a synergistically effective amount.

14 Claims, No Drawings

FOREIGN PATENT DOCUMENTS

| | | |
|---|---|---|
| 0398 692 | 11/1990 | (EP) . |
| 0753 258 | 1/1997 | (EP) . |
| 93/15046 | 8/1993 | (WO) . |
| 96/01256 | 1/1996 | (WO) . |
| 96/10258 | 1/1996 | (WO) . |
| 97/40688 | 11/1997 | (WO) . |
| 98/01033 | 1/1998 | (WO) . |
| 98/08385 | 3/1998 | (WO) . |

FUNGICIDAL MIXTURES

This application is a 371 of PCT/EP98/02,822, filed May 13, 1998.

The present invention relates to a fungicidal mixture which comprises a) a phenyl benzyl ether derivative of the formula I.a, I.b or I.c,

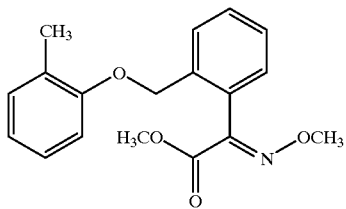
(I.a)

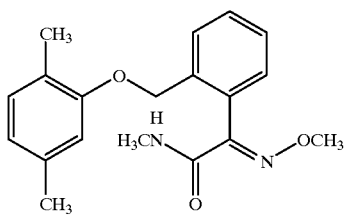
(I.b)

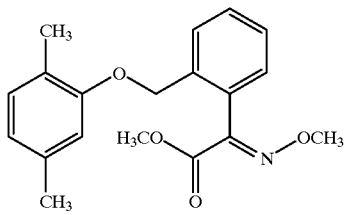
(I.c)

and/or a carbamate of the formula Id

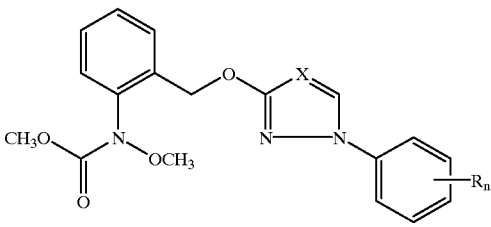
(Id)

where X is CH or N, n is 0, 1 or 2 and R is halogen, $C_1$–$C_4$-alkyl or $C_1$–$C_4$-haloalkyl, it being possible for the radicals R to be different if n is 2, or a salt or adduct thereof,
and
(b) a N-acetonylbenzamide of the formula II

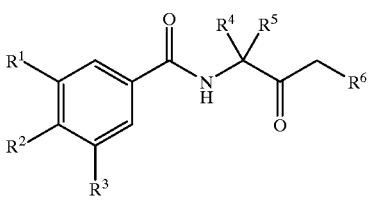
(II)

where:
$R^1$ and $R^3$ independently of one another are each halogen or $C_1$–$C_4$-alkyl;
$R^2$ is cyano, $C_1$–$C_4$-alkyl, $C_2$–$C_4$-alkenyl, $C_2$–$C_4$-alkynyl or $C_1$–$C_4$-alkoxy;
$R^4$ is hydrogen or $C_1$–$C_4$-alkyl;
$R^5$ is $C_2$–$C_4$-alkyl;
$R^6$ is thiocyano, isothiocyano or halogen,
or a salt or adduct thereof,
in a synergistically effective amount.

The invention further relates to methods for controlling harmful fungi using mixtures of the compounds I (I.a, I.b and I.c) and II and to the use of the compound I and the compound II for preparing such mixtures.

The compounds of the formula Ia–c, their preparation and their activity against harmful fungi are known from the literature (EP-A 253 213; EP-A 254 426; EP-A 398 692).

The compounds of the formula Id, their preparation and their activity against harmful fungi are known from the literature (WO-A 93/15,046; WO-A 96/01,256 and WO-A 96/01,258).

Also known are synergistic mixtures of the compounds II with dithiocarbamates, their preparation and their activity against harmful fungi (EP-A 753 258; U.S. Pat. No. 5,304, 572).

It is an object of the present invention to provide mixtures which have an improved activity against harmful fungi combined with a reduced total amount of active ingredients applied (synergistic mixtures), with a view to reducing the application rates and to improving the activity spectrum of the known compounds I and II.

We have found that this object is achieved by the mixture defined at the outset. In addition, we have found that better control of harmful fungi is possible by applying the compound I and the compound II simultaneously, separately as well as together, or by applying the compound I and the compounds II in succession, than when the individual compounds are used.

The formula Id in particular represents carbamates in which the combination of the substituents corresponds to a line of the Table below:

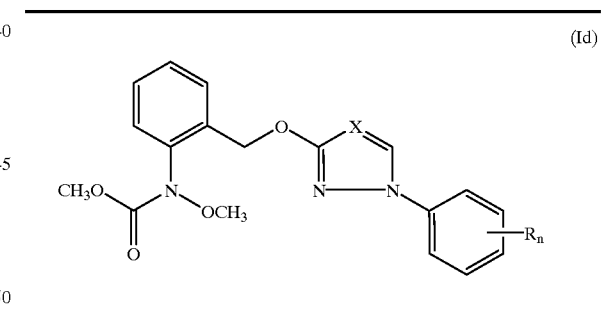
(Id)

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |

-continued

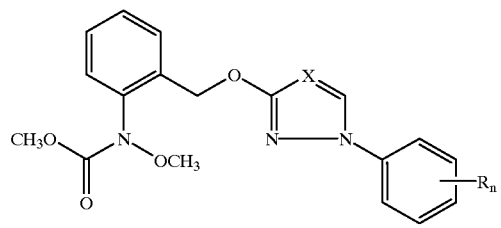

(Id)

| No. | X | $R_n$ |
|---|---|---|
| I.19 | N | 2-CF$_3$ |
| I.20 | N | 3-CF$_3$ |
| I.21 | N | 4-CF$_3$ |
| I.22 | N | 2,4-F$_2$ |
| I.23 | N | 2,4-Cl$_2$ |
| I.24 | N | 3,4-Cl$_2$ |
| I.25 | N | 2-Cl, 4-CH$_3$ |
| I.26 | N | 3-Cl, 4-CH$_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-CH$_3$ |
| I.37 | CH | 3-CH$_3$ |
| I.38 | CH | 4-CH$_3$ |
| I.39 | CH | 2-CH$_2$CH$_3$ |
| I.40 | CH | 3-CH$_2$CH$_3$ |
| I.41 | CH | 4-CH$_2$CH$_3$ |
| I.42 | CH | 2-CH(CH$_3$)$_2$ |
| I.43 | CH | 3-CH(CH$_3$)$_2$ |
| I.44 | CH | 4-CH(CH$_3$)$_2$ |
| I.45 | CH | 2-CF$_3$ |
| I.46 | CH | 3-CF$_3$ |
| I.47 | CH | 4-CF$_3$ |
| I.48 | CH | 2,4-F$_2$ |
| I.49 | CH | 2,4-Cl$_2$ |
| I.50 | CH | 3,4-Cl$_2$ |
| I.51 | CH | 2-Cl, 4-CH$_3$ |
| I.52 | CH | 3-Cl, 4-CH$_3$ |

Particular preference is given to the compounds I.12, I.23, I.32 and I.38.

The formula II in particular represents N-acetonylbenzamides in which the combination of the substituents corresponds to a line of the Table below:

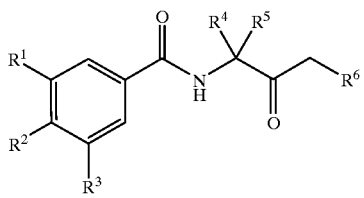

(II)

| No. | R$^1$ | R$^2$ | R$^3$ | R$^4$ | R$^5$ | R$^6$ |
|---|---|---|---|---|---|---|
| II.1 | Cl | CH$_3$ | Cl | CH$_2$CH$_3$ | CH$_3$ | Cl |
| II.2 | Cl | CH$_2$CH$_3$ | Cl | CH$_2$CH$_3$ | CH$_3$ | Cl |
| II.3 | Cl | OCH$_3$ | Cl | CH$_2$CH$_3$ | CH$_3$ | Cl |
| II.4 | Cl | OCH$_2$CH$_3$ | Cl | CH$_2$CH$_3$ | CH$_3$ | Cl |

-continued

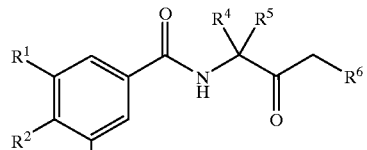

(II)

| No. | R$^1$ | R$^2$ | R$^3$ | R$^4$ | R$^5$ | R$^6$ |
|---|---|---|---|---|---|---|
| II.5 | Cl | CN | Cl | CH$_2$CH$_3$ | CH$_3$ | Cl |
| II.6 | Br | CH$_3$ | Br | CH$_2$CH$_3$ | CH$_3$ | Cl |
| II.7 | Br | CN | Br | CH$_2$CH$_3$ | CH$_3$ | Cl |

Particular preference is given to those N-acetonylbenzamides which are generally and particularly preferred in EP-A 753 258.

Owing to the basic character of their nitrogen atoms, the compounds Id and II are capable of forming adducts or salts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, eg. p-toluenesulfonic acid, dodecylbenzenesulfonic acid, salicylic acid, p-aminosalicylic acid, 2-phenoxybenzoic acid and 2-acetoxybenzoic acid, etc.

Suitable metal ions are, in particular, the ions of the elements of the first to eighth sub-group, in particular chromium, manganese, iron, cobalt, nickel, copper, zinc and of the second main group, in particular calcium and magnesium, and of the third and fourth main group, in particular aluminum, tin and lead. The metals can exist in the various valencies which they can assume.

When preparing the mixtures, it is preferred to employ the pure active ingredients I and II, to which further active ingredients against harmful fungi or other pests, such as insects, arachnids or nematodes, or else herbicidal or glineth-regulating active ingredients or fertilizers can be admixed.

The mixtures of the compounds I and II, or the simultaneous joint or separate use of the compounds I and II, have outstanding action against a wide range of phytopathogenic fungi, in particular from the classes of the Ascomycetes, Basidiomycetes, Phycomycetes and Deuteromycetes. Some of them act systemically and can therefore also be employed as foliar and soil-acting fungicides.

They are specially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: Erysiphe graminis (powdery mildew) in cereals, Erysiphe cichoracearum and Sphaerotheca fuliginea in cucurbits, Podosphaera leucotricha in apples, Uncinula necator in grapevines, Puccinia species in cereals, Rhizoctonia species in cotton, rice and lawns, Ustilago species in cereals and sugar cane, Venturia inaequalis (scab) in apples, Helminthosporium species in cereals, Septoria nodorum in wheat, Botrytis cinerea (gray mold) in strawberries, vegetables, ornamentals and grapevines, Cercospora arachidicola in groundnuts, Pseudocercosporella herpotrichoides in wheat and barley, Pyricularia oryzae in rice, Phytophthora infestans in potatoes and tomatoes, Plasmopara viticola in grapevines, Pseudoperonospora species in hops and cucumbers, Alternaria species in vegetables and fruit, Mycosphaerella species in bananas and Fusarium and Verticillium species.

Furthermore, they can be used in the protection of materials (eg. in the protection of wood), for example against Paecilomyces variotii.

The compounds I and II can be applied simultaneously, that is either together or separately, or in succession, the sequence, in the case of separate application, generally not having any effect on the result of the control measures.

The compounds I and II are usually applied in a weight ratio of 10:1 to 0.01:1, preferably 5:1 to 0.05:1, in particular 1:1 to 0.05:1.

Depending on the nature of the desired effect, the application rates of the mixtures according to the invention are, in particular in agricultural crops, from 0.01 to 8 kg/ha, preferably 0.1 to 5 kg/ha, in particular 0.5 to 3.0 kg/ha.

The application rates of the compounds I are from 0.01 to 2.5 kg/ha, preferably 0.05 to 2.5 kg/ha, in particular 0.05 to 1.0 kg/ha.

Correspondingly, in the case of the compounds II, the application rates are from 0.01 to 10 kg/ha, preferably 0.05 to 5 kg/ha, in particular 0.1 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, to the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene [lacuna], lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC).

The compounds I or II, or the mixtures, or the corresponding formulations, are applied by treating the harmful fungi or the plants, seeds, soils, areas, materials or spaces to be kept free from them with a fungicidally effective amount of the mixture, or of the compounds I and II in the case of separate application.

Application can be effected before or after infection by the harmful fungi.

The synergistic action of the mixtures according to the invention was demonstrated by the following experiments:

Use Example 1—Activity against Phytophthora infestans on tomatoes.

Leaves of plants of the cultivar "GroBe Fleischtomate" in pots were sprayed to run-off with an aqueous suspension made with a stock solution of 10% of active ingredient, 63% of cyclohexanone and 27% of emulsifier. The next day, the leaves were infected with an aqueous zoospore suspension of Phytophthora infestans. The plants were subsequently placed in a water-vapor-saturated chamber at from 16 to 18° C. After 6 days, the tomato blight had developed on the untreated, but infected, control plants to such an extent that it was possible to evaluate the disease level visually in %.

Evaluation was carried out by determining the infected leaf areas in percent. These percentages were converted into degrees of action. The efficacy (E) was calculated as follows using Abbot's formula:

$$E=(1-\alpha)\cdot 100/B$$

α corresponds to the fungal infection of the treated plants in % and

β corresponds to the fungal infection of the untreated (control) plants in %.

A degree of action of 0 means that the infection level of the treated plants corresponds to that of the untreated control plants; a degree of action of 100 means that the treated plants were not infected.

The expected degrees of action of the mixtures of the active ingredients were determined using Colby's formula [R. S. Colby, Weeds 15, (1967) 20–22] and compared with the observed degrees of action.

Colby's formula: $E = x + y - x \cdot y / 100$

E expected degree of action, expressed in % of the untreated control, when using the mixture of the active ingredients A and B at the concentrations of a and b x degree of action, expressed in % of the untreated control, when using active ingredient A at a concentration of a y degree of action, expressed in % of the untreated control, when using active ingredient B at a concentration of b.

The results are shown in Tables 2 and 3 below.

TABLE 2

| Active Ingredient | Concentration of active ingredient in the spray liquor in ppm | Efficacy in % of the untreated control |
|---|---|---|
| Control (untreated) | (100% infection) | 0 |
| Ia | 1 | 0 |
|  | 0.5 | 0 |
|  | 0.25 | 0 |
| Ib | 0.25 | 0 |
| Compound I.32 | 0.25 | 70 |
| Compound II.1 | 0.5 | 20 |
|  | 0.25 | 0 |

TABLE 3

| Mixtures according to the invention | Observed efficacy | Expected efficacy *) |
|---|---|---|
| 1 ppm Ia + 0.25 ppm II.1 | 30 | 0 |
| 0.5 ppm Ia + 0.5 ppm II.1 | 50 | 20 |
| 0.25 ppm Ia + 0.5 ppm II.1 | 40 | 20 |
| 0.25 Ib + 0.5 ppm II.1 | 60 | 20 |
| 0.25 ppm I.32 + 0.5 ppm II.1 | 97 | 76 |

The experimental results reveal that the observed efficacy in all mixing ratios is higher than the efficacy calculated before hand using Colby's formula.

We claim:

1. A composition comprising synergistically effective amounts of a) a phenyl benzyl ether I selected from the group of compounds of formula I.a, I.b and I.c,

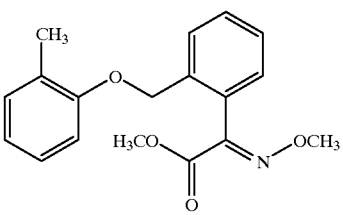

I.a

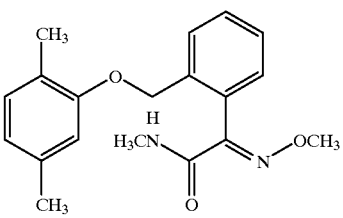

I.b

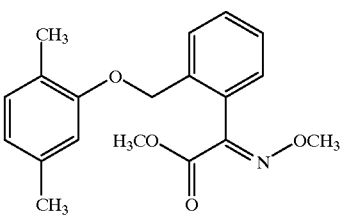

I.c and b) a compound of formula II

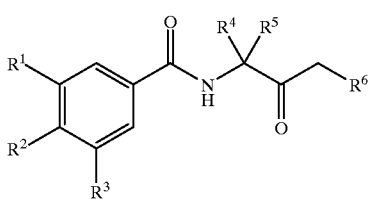

(II)

wherein $R^1$ and $R^3$ independently of one another are each halogen or $C_1$–$C_4$-alkyl;

$R^2$ is cyano, $C_1$–$C_4$-alkyl, $C_2$–$C_4$-alkenyl, $C_2$–$C_4$-alkynyl or $C_1$–$C_4$-alkoxy;

$R^4$ is hydrogen or $C_1$–$C_4$-alkyl;

$R^5$ is $C_2$–$C_4$-alkyl;

$R^6$ is thiocyano, isothiocyano or halogen, or a salt or adduct thereof.

2. The composition defined in claim 1, wherein the phenyl benzyl ether I and the compound of formula II or its salt or adduct are present in a weight ratio of from 10:1 to 0.01:1.

3. The composition defined in claim 1 which is conditioned in two parts, one part comprising the phenyl benzyl ether I in a solid or liquid carrier and the other part comprising the compound of formula II or its salt or adduct in a solid or liquid carrier.

4. The composition defined in claim 1, wherein component (a) is a combination of the phenyl benzyl ether I and a carbamate of formula Id

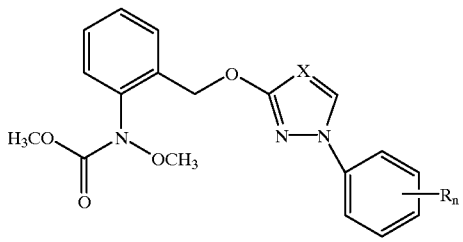

(Id)

wherein X is CH or N, n is 0, 1 or 2 and R is halogen, $C_1$–$C_4$-alkyl or $C_1$–$C_4$-haloalkyl, and where the radicals R are identical or different when n is 2, or a salt or adduct thereof.

5. The composition defined in claim 4, wherein component (a) and the compound of formula II or its salt or adduct are present in a weight ratio of from 10:1 to 0.01:1.

6. The composition defined in claim 4 which is conditioned in two parts, one part comprising component (a) in a solid or liquid carrier and the other part comprising the compound of formula II or its salt or adduct in a solid or liquid carrier.

7. A method for controlling harmful fungi, which comprises treating the harmful fungi, their habitat, or plants, seeds, soils, areas, materials or spaces to be kept free from the fungi with synergistically effective amounts of a) a phenyl benzyl ether I selected from the group of compounds of formula I.a, I.b and I.c,

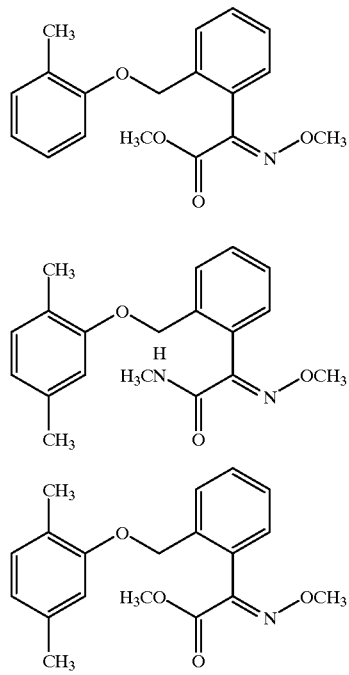

I.a

I.b

I.c and b) a compound of formula II

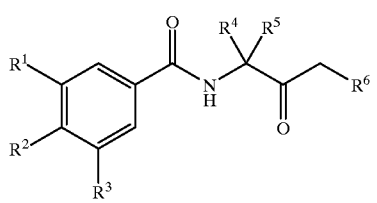

(II)

wherein $R^1$ and $R^3$ independently of one another are each halogen or $C_1$–$C_4$-alkyl;

$R^2$ is cyano, $C_1$–$C_4$-alkyl, $C_2$–$C_4$-alkenyl, C2–$C_4$-alkynyl or $C_1$–$C_4$-alkoxy;

$R^4$ is hydrogen or $C_1$–$C_4$-alkyl;

$R^5$ is $C_2$–$C_4$-alkyl;

$R^6$ is thiocyano, isothiocyano or halogen, or a salt or adduct thereof.

8. The method of claim 7, wherein the phenyl benzyl ether I and the compound of formula II or its salt or adduct are applied simultaneously, separately or together, or in succession.

9. The method of claim 7, wherein the the phenyl benzyl ether I is applied in an amount of from 0.01 to 2.5 kg/ha.

10. The method of claim 7, wherein the compound of formula II or its salt or adduct is applied in an amount of from 0.01 to 10 kg/ha.

11. The method of claim 7, wherein component (a) is a combination of the phenyl benzyl ether I and a carbamate of formula Id

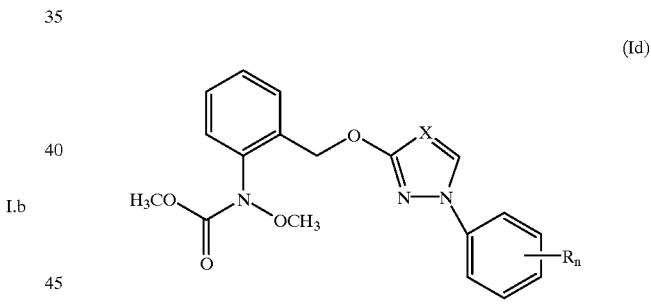

(Id)

wherein X is CH or N, n is 0, 1 or 2 and R is halogen, $C_1$–$C_4$-alkyl or $C_1$–$C_4$-haloalkyl, and where the radicals R are identical or different when n is 2, or a salt or adduct thereof.

12. The method of claim 11, wherein component (a) and the compound of formula II or its salt or adduct are applied simultaneously, separately or together, or in succession.

13. The method of claim 11, wherein component (a) is applied in an amount of from 0.01 to 2.5 kg/ha.

14. The method of claim 11, wherein the compound of formula II or its salt or adduct is applied in an amount of from 0.01 to 10 kg/ha.

* * * * *

UNITED STATES PATENT AND TRADEMARK OFFICE
CERTIFICATE OF CORRECTION

PATENT NO.     : 6,291,497 B1                                    Page 1 of 1
DATED          : September 18, 2001
INVENTOR(S)    : Schelberger et al.

It is certified that error appears in the above-identified patent and that said Letters Patent is hereby corrected as shown below:

<u>Column 10, claim 7,</u>
Line 17, "C2-$C_4$-" should be -- $C_2$-$C_4$- --.

Signed and Sealed this

Twenty-sixth Day of February, 2002

Attest:

JAMES E. ROGAN
Attesting Officer    Director of the United States Patent and Trademark Office